(12) United States Patent
Reggiani et al.

(10) Patent No.: US 8,980,176 B2
(45) Date of Patent: *Mar. 17, 2015

(54) BLOOD PROCESSING UNIT WITH CROSS BLOOD FLOW

(75) Inventors: Stefano Reggiani, Medolla (IT); Claudio Giovannini, Carbonara di Po (IT); Claudio Silvestri, Quarantoli Mirandola (IT); Gabriele Tommasi, Cavezzo (IT)

(73) Assignee: Sorin Group Italia S.r.l., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/110,122

(22) Filed: May 18, 2011

(65) Prior Publication Data

US 2012/0294761 A1 Nov. 22, 2012

(30) Foreign Application Priority Data

May 17, 2011 (EP) .................................... 11166394

(51) Int. Cl.
*A61M 1/00* (2006.01)
*A61M 1/16* (2006.01)
*B01D 63/02* (2006.01)
*F28F 21/06* (2006.01)

(52) U.S. Cl.
CPC ......... *A61M 1/1698* (2013.01); *A61M 2206/20* (2013.01); *B01D 63/02* (2013.01); *B01D 2313/38* (2013.01); *Y10S 261/28* (2013.01); *F28F 21/062* (2013.01); *A61M 1/1629* (2014.02)
USPC .................... 422/46; 422/44; 422/45; 422/47; 422/48; 261/DIG. 28

(58) Field of Classification Search
CPC .......... A61M 1/1698; A61M 2206/20; A61M 1/1629; B01D 2313/38; B01D 63/02; F28F 21/062; Y10S 261/28
USPC .................................... 422/44, 45, 46, 47, 48
See application file for complete search history.

(56) References Cited

U.S. PATENT DOCUMENTS

| 3,957,648 | A |   | 5/1976 | Roget et al. |
| 4,038,190 | A |   | 7/1977 | Baudet et al. |
| 4,229,305 | A |   | 10/1980 | Fecondini et al. |
| 4,597,868 | A |   | 7/1986 | Watanabe |
| 4,639,353 | A |   | 1/1987 | Takemura et al. |
| 4,902,476 | A | * | 2/1990 | Gordon et al. .................. 422/46 |
| 5,169,530 | A |   | 12/1992 | Schucker et al. |

(Continued)

FOREIGN PATENT DOCUMENTS

| EP | 0312125 A1 | 4/1989 |
| EP | 0582959 A1 | 2/1994 |

(Continued)

OTHER PUBLICATIONS

European Search Report issued in EP Application No. 10161451, dated Sep. 28, 2010, 5 pages.

(Continued)

Primary Examiner — Tatyana Zalukaeva
Assistant Examiner — Andrew J Mensh
(74) Attorney, Agent, or Firm — Faegre Baker Daniels LLP

(57) ABSTRACT

A blood processing apparatus may include a heat exchanger and a gas exchanger. The heat exchanger may be configured to provide a cross-flow or radially directed blood flow through the heat exchanger.

8 Claims, 7 Drawing Sheets

(56) References Cited

U.S. PATENT DOCUMENTS

| | | | |
|---|---|---|---|
| 5,192,439 A * | 3/1993 | Roth et al. | 210/485 |
| 5,192,499 A | 3/1993 | Sakai et al. | |
| 5,270,004 A | 12/1993 | Cosentino et al. | |
| 5,316,724 A | 5/1994 | Mathewson et al. | |
| 5,338,512 A | 8/1994 | Mathewson et al. | |
| 5,514,095 A * | 5/1996 | Brightbill et al. | 604/113 |
| 5,578,267 A | 11/1996 | Cosentino et al. | |
| 5,674,452 A | 10/1997 | Carson et al. | |
| 5,733,398 A | 3/1998 | Carson et al. | |
| 5,762,868 A | 6/1998 | Leonard | |
| 5,762,869 A | 6/1998 | White et al. | |
| 5,817,278 A | 10/1998 | Fini et al. | |
| 5,817,279 A | 10/1998 | Eilers et al. | |
| 5,830,370 A * | 11/1998 | Maloney et al. | 210/780 |
| RE36,774 E | 7/2000 | Cosentino et al. | |
| 6,105,664 A | 8/2000 | Gillbrand et al. | |
| 6,113,782 A | 9/2000 | Leonard | |
| 6,241,945 B1 | 6/2001 | Owen | |
| 6,454,999 B1 | 9/2002 | Farhangia et al. | |
| 6,755,894 B2 | 6/2004 | Bikson et al. | |
| 6,960,322 B2 | 11/2005 | Stringer et al. | |
| 8,318,092 B2 | 11/2012 | Reggiani et al. | |
| 8,388,566 B2 | 3/2013 | Reggiani et al. | |
| 8,394,049 B2 | 3/2013 | Reggiani et al. | |
| 8,652,406 B2 | 2/2014 | Reggiani et al. | |
| 8,795,220 B2 | 8/2014 | Reggiani et al. | |
| 2002/0039543 A1 | 4/2002 | Ikeda et al. | |
| 2003/0080047 A1 | 5/2003 | Watkins et al. | |
| 2004/0175292 A1 | 9/2004 | Ghellil et al. | |
| 2004/0251011 A1 | 12/2004 | Kudo | |
| 2007/0107884 A1 | 5/2007 | Sirkar et al. | |
| 2007/0166190 A1 | 7/2007 | Ogihara et al. | |
| 2007/0231203 A1 | 10/2007 | Mizoguchi et al. | |
| 2008/0234623 A1 | 9/2008 | Strauss et al. | |
| 2010/0269342 A1 | 10/2010 | Carpenter et al. | |
| 2010/0272606 A1 | 10/2010 | Carpenter et al. | |
| 2010/0272607 A1 | 10/2010 | Carpenter et al. | |
| 2011/0268608 A1 | 11/2011 | Reggiani et al. | |
| 2011/0268609 A1 | 11/2011 | Reggiani et al. | |
| 2012/0046594 A1 | 2/2012 | Reggiani et al. | |
| 2012/0121463 A1 | 5/2012 | Reggiani et al. | |
| 2013/0142695 A1 | 6/2013 | Reggiani et al. | |
| 2013/0142696 A1 | 6/2013 | Reggiani et al. | |
| 2014/0227133 A1 | 8/2014 | Reggiani et al. | |

FOREIGN PATENT DOCUMENTS

| | | |
|---|---|---|
| EP | 0895786 A1 | 2/1999 |
| EP | 1108462 A2 | 6/2001 |
| EP | 1180374 A1 | 2/2002 |
| EP | 1371381 A1 | 12/2003 |
| EP | 1834656 B1 | 9/2007 |
| JP | 2007190218 A | 2/2007 |
| WO | WO9716213 A2 | 5/1997 |
| WO | WO9719714 A1 | 6/1997 |
| WO | WO9733636 A1 | 9/1997 |
| WO | WO2010124087 A1 | 10/2010 |

OTHER PUBLICATIONS

European Search Report issued in EP Application No. 10173436, dated Feb. 14, 2011, 7 pages.
European Search Report issued in EP Application No. 10186550, dated Jan. 27, 2011, 7 pages.
International Search Report issued in PCT/IB2011/054725, mailed Feb. 9, 2012, 12 pages.
International Search Report and Written Opinion issued in PCT/IB2012/052424, mailed Oct. 24, 2012, 17 pages.
European Search Report issued in EP Application No. 10191140, mailed Nov. 30, 2011, 8 pages.
European Search Report issued in EP Application No. 12187501, mailed Nov. 20, 2013, 6 pages.
European Search Report issued in EP Application No. 13161841, mailed Jun. 11, 2013, 6 pages.

* cited by examiner

BLOOD PROCESSING UNIT WITH CROSS BLOOD FLOW

CROSS-REFERENCE TO RELATED APPLICATION

This application claims priority to European Application No. EP11166394.4, filed May 17, 2011, under 35 U.S.C. §119, which is herein incorporated by reference in its entirety. This application is related to U.S. patent application Ser. No. 12/860,062, filed Aug. 20, 2010, entitled "Blood Processing Unit with Modified Flow Path," and U.S. patent application Ser. No. 12/947,171, filed Nov. 16, 2010, entitled "Blood Processing Unit with Circumferential Blood Flow," each of which are hereby incorporated by reference in its entirety.

BACKGROUND

Blood perfusion entails encouraging blood through the vessels of the body. For such purposes, blood perfusion systems typically entail the use of one or more pumps in an extracorporeal circuit that is interconnected with the vascular system of a patient. Cardiopulmonary bypass surgery typically requires a perfusion system that provides for the temporary cessation of the heart to create a still operating field by replacing the function of the heart and lungs. Such isolation allows for the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures oxygen-poor blood, i.e., venous blood, is gravity-drained or vacuum suctioned from a large vein entering the heart or other veins in the body (e.g., femoral) and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is filtered and then returned through an arterial line to the aorta, femoral artery, or other artery.

SUMMARY

Example 1 is a blood processing apparatus including a housing having a blood inlet and a blood outlet, the blood inlet extending into an interior of the housing, a heat exchanger core extending coaxially within the housing and having a core interior in fluid communication with the blood inlet, the heat exchanger core including an outer surface and at least one pair of elongate core apertures formed within the outer surface, the pair of elongate core apertures configured to permit blood to pass from the core interior, the heat exchanger hollow fibers disposed about the heat exchanger core such that a heat exchanger fluid may flow through the heat exchanger hollow fibers and blood passing from the plurality of elongate core apertures may flow radially outwardly across the heat exchanger hollow fibers, a cylindrical shell extending coaxially about the heat exchanger core, the cylindrical shell including a shell aperture configured to permit blood to pass to an exterior of the cylindrical shell; and gas exchanger hollow fibers disposed about the inner cylindrical shell such that gases may flow through the gas exchange hollow fibers and blood passing from the shell aperture may flow across the gas exchanger hollow fibers and towards the blood outlet.

Example 2 is the blood processing apparatus of Example 1 wherein the heat exchanger core includes three pair of elongate core apertures radially disposed at approximately equal distances about a circumference of the core.

Example 3 is the blood processing apparatus of any preceding Example wherein the plurality of elongate core apertures are arranged in pairs.

Example 4 is the blood processing apparatus of any preceding Example wherein the plurality of elongate core apertures comprise a total of four equally spaced pairs of elongate core apertures.

Example 5 is the blood processing apparatus of any preceding Example wherein each pair of elongate core apertures comprise a first elongate channel and a second elongate channel separated by an elongate dividing plate extending between the first elongate core aperture and the second elongate core aperture.

Example 6 is the blood processing apparatus of any preceding Example wherein each of the first and second elongate channels have a floor surface disposed at an angle with respect to a longitudinal axis of the core, such that the depth of the channel decreases as blood flows longitudinally along the core.

Example 7 is the blood processing apparatus of any preceding Example wherein the outer surface of the heat exchanger core includes a plurality of radially disposed ribs.

Example 8 is the blood processing apparatus of any preceding Example wherein the shell aperture comprises an elongate shell aperture positioned diametrically opposed to the blood outlet such that blood exiting the elongate shell aperture flows across the gas exchanger hollow fibers in a circumferential direction.

Example 9 is the blood processing apparatus of any preceding Example wherein the shell aperture comprises a radially disposed aperture disposed near an end of the cylindrical shell opposite that of the blood inlet such that blood exiting the radially disposed aperture flows over the gas exchanger hollow fibers in a longitudinal direction.

Example 10 is the blood processing apparatus of any preceding Example further comprising an annular collection space between the heat exchanger hollow fibers and the cylindrical shell, the annular collection space in fluid communication with the shell aperture.

Example 11 is a blood processing apparatus including a housing having a blood inlet and a blood outlet, the blood inlet extending into an interior of the housing, a heat exchanger core extending within the housing and having a core interior in fluid communication with the blood inlet, the heat exchanger core including an outer surface and a plurality of elongate core apertures formed within the outer surface, the plurality of elongate core apertures configured to permit blood to pass from the core interior, the heat exchanger hollow fibers arranged in a bundle such that blood passing from the plurality of elongate core apertures may pass straight across the heat exchanger hollow fibers, a collection space upstream of the heat exchanger hollow fibers, the collection space arranged to collect blood that has passed across the heat exchanger hollow fibers, and gas exchanger hollow fibers disposed about the collection space such that gases may flow through the gas exchange hollow fibers and blood passing from the collection space may flow across the gas exchanger hollow fibers and towards the blood outlet.

Example 12 is the blood processing apparatus of Example 11 wherein blood flow across the gas exchanger hollow fibers is in a circumferential direction.

Example 13 is the blood processing apparatus of any of Examples 11-12 wherein the housing has a triangular cross-sectional profile to accommodate the bundle of heat exchanger hollow fibers.

Example 14 is the blood processing apparatus of any of Examples 11-13 wherein the heat exchanger core comprises a grid that supports the bundle of heat exchanger hollow fibers on the grid as well as providing a plurality of outlets for blood to exit the interior of the heat exchanger core.

Example 15 is the blood processing apparatus of any of Examples 11-14 wherein the bundle of heat exchanger hollow fibers are wrapped about the grid.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

The disclosure pertains to a blood processing apparatus that, according to various exemplary embodiments, includes one or more of a heat exchanger and a gas exchanger (also commonly referred to as an oxygenator). In some embodiments, the term oxygenator may be used to refer to an integrated structure that combines a heat exchanger and a gas exchanger in a unitary device. In various embodiments, for example, the heat exchanger and gas exchanger are disposed in a concentric fashion with one component located inside of the other component. According to other embodiments, the heat exchanger and gas exchanger are structurally distinct structures operable coupled to each other. In some embodiments, an oxygenator may be used in an extracorporeal blood circuit. An extracorporeal blood circuit, such as may be used in a bypass procedure, may include several different elements such as a heart-lung machine, a blood reservoir, as well as an oxygenator.

Figure 1:
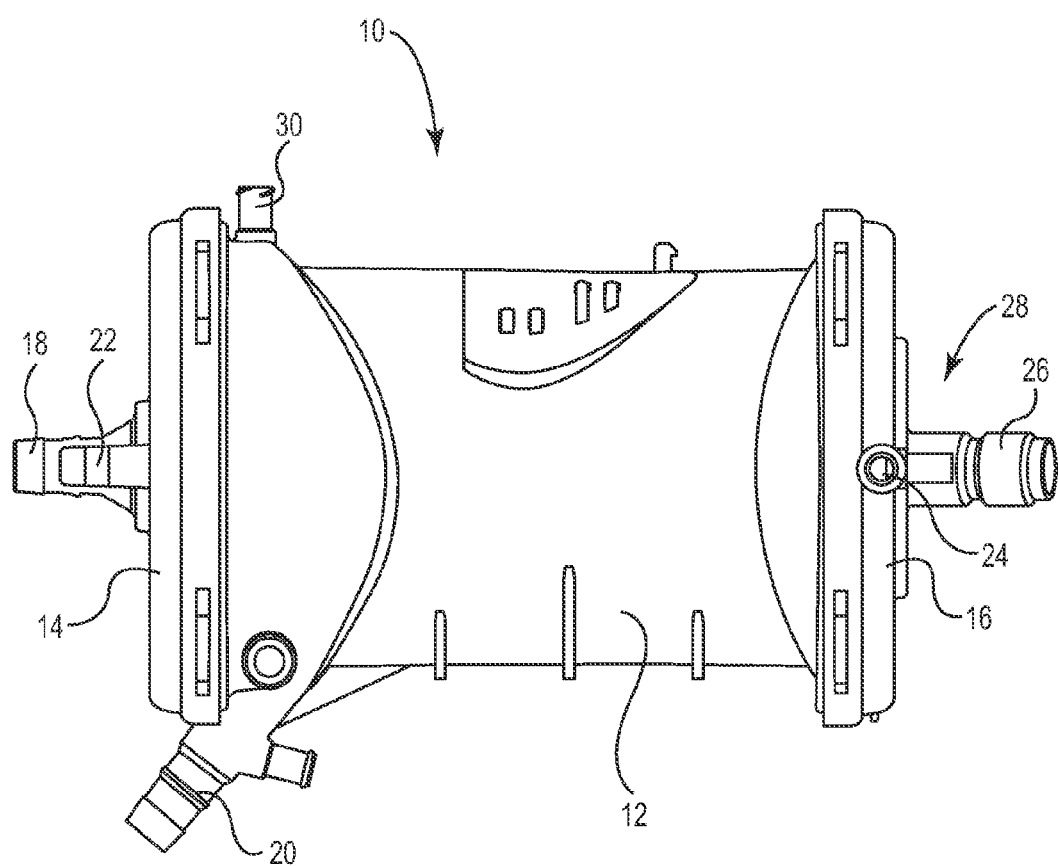
FIG. 1 is a schematic illustration of a blood processing apparatus in accordance with an embodiment of the invention.

FIG. 1 is a schematic illustration of a blood processing apparatus or oxygenator 10. While the internal components are not visible in this illustration, the oxygenator 10 may include one or more of a heat exchanger and a gas exchanger. According to some embodiments, the heat exchanger and the gas exchanger are integrated into a single structure that forms an oxygenator housing. The oxygenator 10 includes a housing 12, a first end cap 14 that is secured to the housing 12 and a second end cap 16 that is secured to the housing 12. In some embodiments, the housing 12 may include other structure that enables attachment of the housing 12 to other devices. While the housing 12 is illustrated as largely cylindrical in shape, in some embodiments, the housing 12 may have a triangular, rectangular or other parallelogram cross-sectional shape. Each of the heat exchanger and the gas exchanger may have generally the same sectional shape or each may have a different sectional shape. In some embodiments, the heat exchanger may be inside the gas exchanger while in other embodiments the gas exchanger may be located within the heat exchanger. In some embodiments, the heat exchanger and the gas exchanger may be concentric.

In some embodiments, a blood inlet 18 extends into the housing 12 and a blood outlet 20 exits the housing 12. As noted, in some embodiments the blood processing apparatus 10 includes a gas exchanger and thus may include a gas inlet 22 and a gas outlet 24. In some embodiments, the blood processing apparatus 10 includes a heat exchanger and thus may include a heat exchanger fluid inlet 26 and a heat exchanger fluid outlet 28 that is behind (in the illustrated orientation) the heating fluid inlet 26. In some embodiments, the heat exchanger fluid inlet 26 may be disposed at one end of the housing 12 while the heat exchanger fluid outlet 28 may be disposed at an opposite end of the housing 12. In some embodiments, the blood processing apparatus 10 may include one or more purge ports 30 that may be used for purging air bubbles from the interior of the blood processing apparatus 10.

The positions of the inlets, outlets and purge port are merely illustrative, as other arrangements and configurations are contemplated. The purge port may include a valve or a threaded cap. The purge port operates to permit gases (e.g., air bubbles) that exit the blood to be vented or aspirated and removed from the blood processing apparatus 10.

Figure 2:
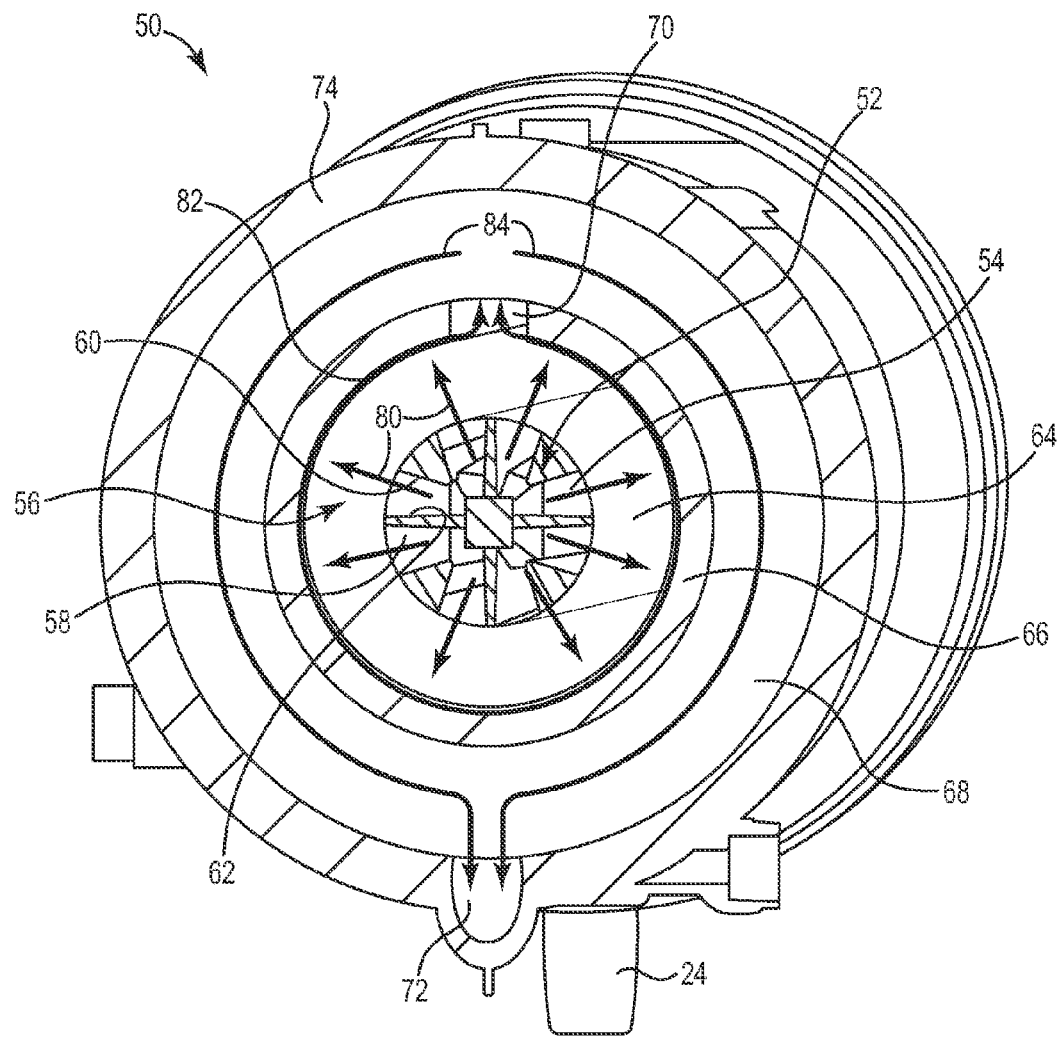
FIGS. 2-4 are sectional views of a blood processing apparatus in accordance with various embodiments of the invention.

FIG. 2 is a sectional view of a blood processing apparatus 50 in which blood flow through the heat exchanger portion is in a radially-outward direction and blood flow through the gas exchanger portion is circumferential. The blood processing apparatus 50 includes a heat exchanger core 52, a heat exchanger element 64 and a gas exchanger element 68. Blood enters an interior volume of the heat exchanger core 52 through the blood inlet 18 (not shown in FIG. 2). The heat exchanger core 52 includes a plurality of elongate core apertures 54 that permit blood to exit the heat exchanger core 52.

In some embodiments, as illustrated, the plurality of elongate core apertures 54 are arranged into pairs 56, with each pair 56 including a first elongate core aperture 58 and a second elongate core aperture 60. In some embodiments, each pair 56 also includes a dividing plate 62 that is disposed between the first elongate core aperture 58 and the second elongate core aperture 60 and that may be configured to guide or direct blood flow. In some embodiments, as illustrated, the pairs 56 are equally spaced about the heat exchanger core 52. In some embodiments, there may be a total of four equally spaced pairs 56. In some embodiments, the pairs 56 may not be equally spaced and/or the plurality of elongate core apertures 54 may not be arranged in pairs. As shown for example by the arrows 80 in FIG. 2, blood exiting the plurality of elongate core apertures 54 flows in a radially-outward direction through a heat exchanger element 64.

The blood processing apparatus 50 includes a cylindrical shell 66 that delineates the heat exchanger element 64 from a gas exchanger element 68. In some embodiments, the cylindrical shell 66 includes an elongate shell aperture 70 that permits blood to flow into the gas exchanger element 68. As shown for example by the arrows 82 in FIG. 2, blood reaching the cylindrical shell 66 is deflected such that it flows in a generally circumferential manner toward the aperture 70. In some embodiments, the elongate shell aperture 70 permits blood to flow through the gas exchanger element 68 in a circumferential direction. In some embodiments, as illustrated, the elongate shell aperture 70 may be diametrically opposed to a blood outlet 72, thereby guiding blood to flow through the gas exchanger element 68 in a circumferential direction, as shown for example by the arrows 84 in FIG. 2. The blood processing apparatus 50 includes an outer housing 74.

In some embodiments, the heat exchanger element 64 includes a number of hollow fibers through which a heating fluid such as water can flow. The blood may flow around and past the hollow fibers and thus be suitably heated. In some embodiments, the hollow fibers may be polymeric. In some cases, metallic fibers may be used. In some embodiments, the hollow fibers may be formed of polyurethane, polyester, or any other suitable polymer or plastic material. According to various embodiments, the hollow fibers have an outer diameter of between about 0.2 and 1.0 millimeters or, more specifically, between about 0.25 and 0.5 millimeters. The hollow fibers may be woven into mats that can range, for example, from about 80 to about 200 millimeters in width. In some embodiments, the mats are arranged in a criss-cross configuration.

In some embodiments the gas exchanger element 68 may include a number of microporous hollow fibers through which a gas such as oxygen may flow. The blood may flow around and past the hollow fibers. Due to concentration gradients, oxygen may diffuse through the microporous hollow fibers into the blood while carbon dioxide may diffuse into the hollow fibers and out of the blood. In some embodiments, the hollow fibers are made of polypropylene, polyester, or any other suitable polymer or plastic material. According to various embodiments, the hollow fibers have an outer diameter of about 0.38 millimeters. According to other embodiments, the microporous hollow fibers having a diameter of between about 0.2 and 1.0 millimeters, or more specifically, between about 0.25 and 0.5 millimeters. The hollow fibers may be woven into mats that can range, for example, from about 80 to about 200 millimeters in width. In some embodiments, the mats are in a criss-cross configuration.

Figure 3:
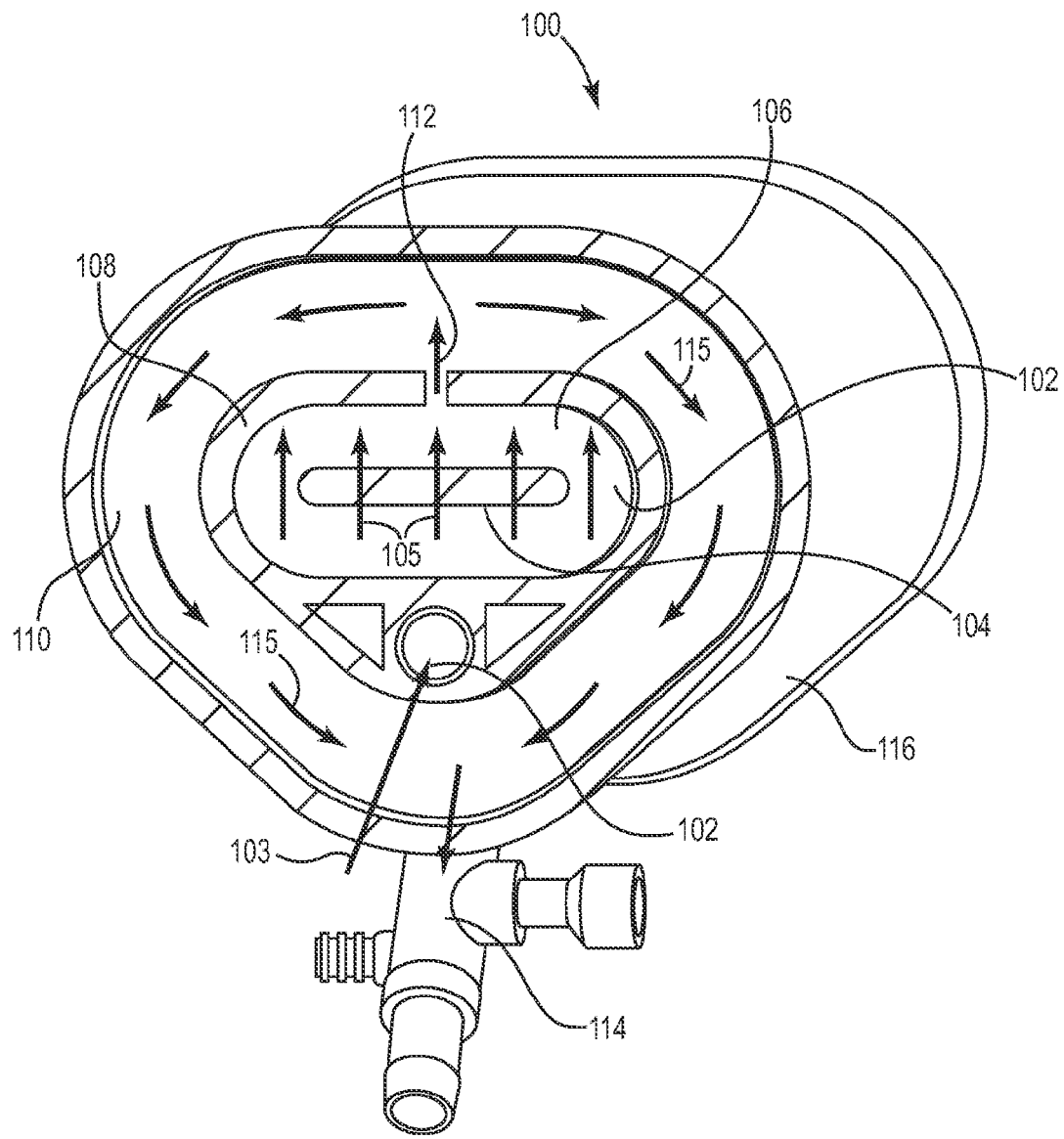

FIG. 3 is a cross-sectional view of a blood processing apparatus 100 in which blood flow through the heat exchanger portion is linear while blood flow through the gas exchanger portion is circumferential. The blood processing apparatus 100 includes a blood inlet 102, which is fluidly coupled to a heat exchanger core 104. Blood flowing into the inlet 102 (shown for example by arrow 103 in FIG. 3) enters an interior volume of the heat exchanger core 104. The heat exchanger core 104 includes apertures or opening arranged (e.g., in a grid structure) to permit blood to exit the interior volume of the core 104 in a plurality of streams. Blood exits the core 104 and flows in a linear or cross-flow manner (as shown for example by arrows 105 in FIG. 3) through the heat exchanger element 106, which includes bundled heat exchanger hollow fibers that may be constructed as discussed above with respect to the heat exchanger element 64.

The blood processing apparatus 100 includes a shell 108 that delineates the heat exchanger element 106 from a gas exchanger element 110. In some embodiments, as illustrated, the shell 108 has a triangular cross-sectional profile to accommodate the heat exchanger core 102 and the heat exchanger element 106. In other embodiments, other shapes are also contemplated.

In some embodiments, the shell 108 includes an elongate shell aperture 112 that permits blood to flow into the gas exchanger element 110. In some embodiments, the elongate shell aperture 112 permits blood to flow through the gas exchanger element 110 in a circumferential direction. In some embodiments, as illustrated, the elongate shell aperture 112 may be diametrically opposed to a blood outlet 114, thereby guiding blood to flow through the gas exchanger element 110 in a circumferential direction, as shown for example by the arrows 115 in FIG. 3. The blood processing apparatus 100 includes an outer housing 116 that may be complementary in shape to the heat exchanger core 102. The gas exchanger element 110 may be constructed of hollow fibers as discussed above with respect to the gas exchanger element 68.

Figure 4:
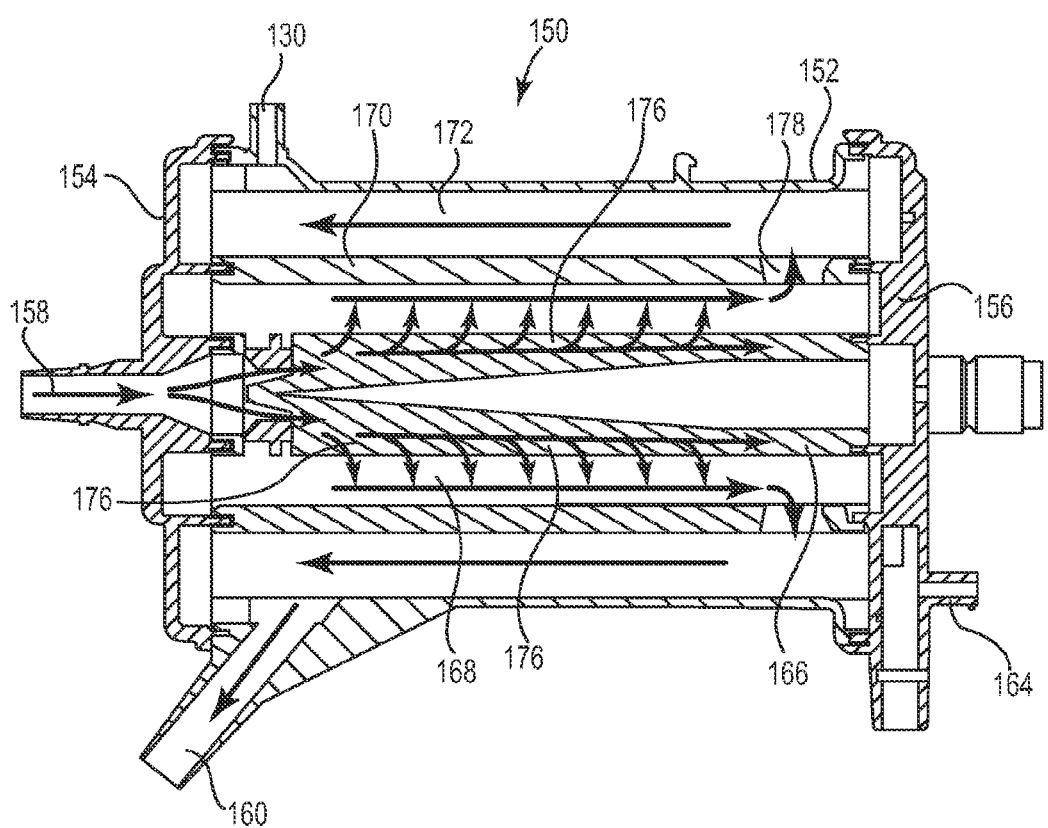

FIG. 4 is a cross-sectional view of a blood processing apparatus 150 in which blood flow through the heat exchanger portion is partially radially outward and partially longitudinal while blood flow through the gas exchanger portion is longitudinal. The blood processing apparatus 150 includes a housing 152, a first end cap 154 and a second end cap 156. The blood processing apparatus 150 includes a blood inlet 158 and a blood outlet 160. A gas inlet (not visible in this cross-section) permits oxygen to be provided to the gas exchanger portion while a gas outlet 164 permits gases to exit the blood processing apparatus 150. In some embodiments, the blood processing apparatus 150 includes a purge port 130 to permit air bubbles to escape.

The blood processing apparatus 150 includes a heat exchanger core 166, a heat exchanger element 168 disposed about the heat exchanger core 166, a cylindrical shell 170 disposed about the heat exchanger element 168 and a gas exchanger element 172. The heat exchanger element 168 and the gas exchanger element 172 may each include a number of hollow fibers as discussed with respect to the blood processing apparatus 150.

In use, blood enters through the blood inlet 158 and passes into the heat exchanger core 166. The blood fills the heat exchanger core 166 and exits through a plurality of elongate core apertures 176 and thus enters the heat exchanger element 168. After blood passes through the heat exchanger element 168, the blood exits the cylindrical shell 170 through a radially disposed shell aperture 178. In some embodiments, the radially disposed shell aperture 178 may be located near an end of the blood processing apparatus 150 that is opposite the blood outlet 160, thereby causing the blood flowing around and past the gas exchanger element 172 in a longitudinal direction. Blood then exits the blood processing apparatus 150 through the blood outlet 160.

Figure 5:
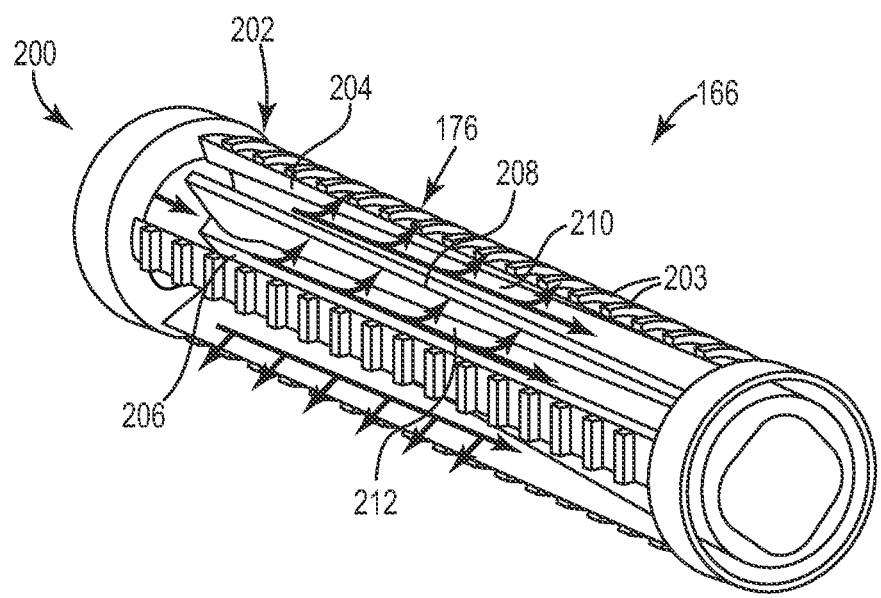
FIGS. 5-7 are perspective views of portions of a blood processing apparatus in accordance with various embodiments of the invention.

FIG. 5 is a perspective view of the heat exchanger core 166. Blood enters the heat exchanger core 166 through an inlet 200. In some embodiments, as illustrated, the elongate core aperture 176 may be part of a more complicated structure 202. The heat exchanger core 166 may include one, two, three or more distinct structures 202 disposed about the heat exchanger core 166. The structure 202 includes a first elongate channel 204 and a second elongate channel 206. A dividing plate 208 is disposed between the first elongate channel 204 and the second elongate channel 206. In some embodiments, the first elongate channel 204 has a sloping floor 210 and/or the second elongate channel 206 has a sloping floor 212. In some embodiments, the structure 202 includes a plurality of radially disposed ribs 203. According to various embodiments the first elongate channel 204 and the second elongate channel 206 are formed with a floor disposed at an angle with respect to a longitudinal axis of the core, such that as the floor extends longitudinally away from the blood inlet, the depth of the channel decreases. According to some embodiments, the angle of the floor 210 with respect to the longitudinal axis is between about 5 and about 30 degrees. In some embodiments, the angle of the floor 210 with respect to the longitudinal axis is between about 10 and about 20 degrees. According to some embodiments, the angles of the floor 210 of the first elongate channel 204 and the floor 210 of the second elongate channel 206 are substantially identical. According to other embodiments the angles of the floor 210 of the first elongate channel 204 and the floor 210 of the second elongate channel 206 are different.

In some embodiments, the structure 202 may help guide blood flow through the heat exchanger element 168 (FIG. 4) in a partially radially-outward, partially longitudinal direction. The ratio of radial (i.e., outward or cross) flow to longitudinal flow depends on a length and an angle of each of the elongate channel 204 and the elongate channel 206. According to various embodiments, the ribs 203 may be substantially perpendicular to the longitudinal axis of the core. In other embodiments, the ribs 230 may be disposed at an angle offset from perpendicular. According to various embodiments, the ribs 203 may protrude or extend radially outward a distance of between about 2 and about 5 mm. According to other embodiments of the invention, the core 166 may include more elongate channels, such that blood may exit at more locations about a circumference of the core 166.

Figure 6:
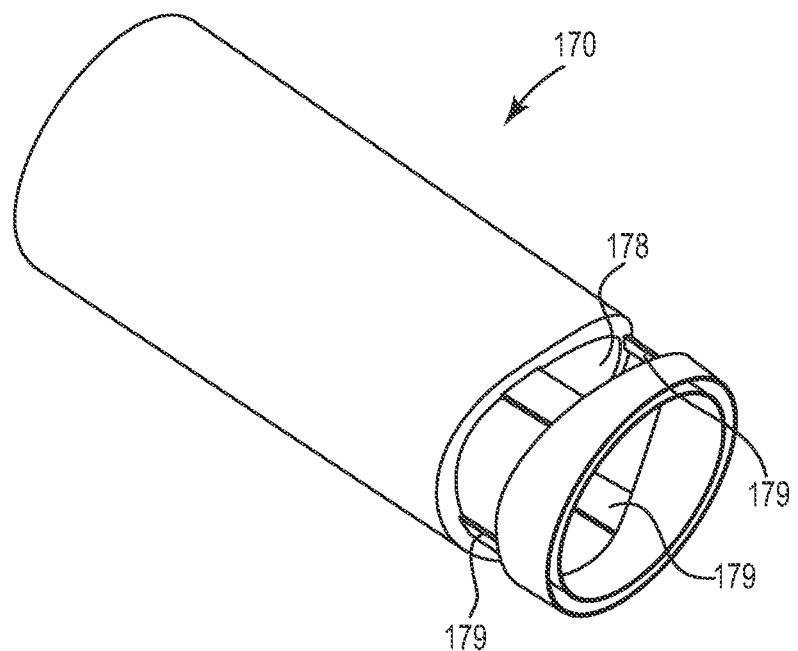

FIG. 6 is a perspective view of the cylindrical shell 170, illustrating the radially disposed shell aperture 178. In some embodiments, as illustrated, the radially disposed shell aperture 178 extends a substantial way around the cylindrical shell 170. In the illustrated embodiment, the radially disposed shell aperture 178 extends all the way around the cylindrical shell 170 except for three small supports 179 that extend across the radially disposed shell aperture 178.

Figure 7:
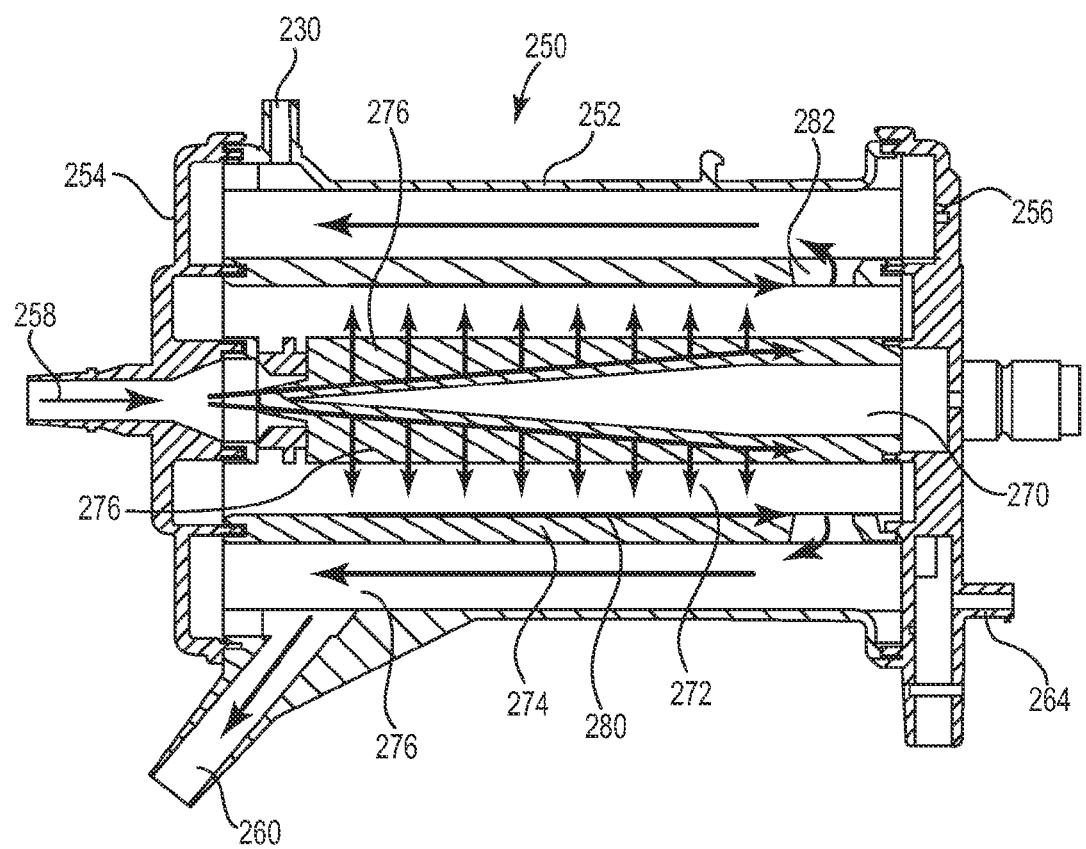

FIG. 7 is a cross-sectional view of a blood processing apparatus 250 in which blood flow through the heat exchanger portion is cross-flow, while blood flow through the gas exchanger portion is longitudinal. The blood processing apparatus 250 includes a housing 252, a first end cap 254 and a second end cap 256. The blood processing apparatus 250 includes a blood inlet 258 and a blood outlet 260. A gas inlet (not visible) permits oxygen to be provided to the gas exchanger portion while a gas outlet 264 permits gases to exit the blood processing apparatus 150. In some embodiments, the blood processing apparatus 250 includes a purge port 230 to permit air bubbles to escape.

The blood processing apparatus 250 includes a heat exchanger core 270, a heat exchanger element 272 disposed about the heat exchanger core 270, a cylindrical shell 274 disposed about the heat exchanger element 272 and a gas exchanger element 276 disposed about the cylindrical shell 274. The heat exchanger element 272 and the gas exchanger element 276 may each include a number of hollow fibers as discussed with respect to the blood processing apparatus 50. In some embodiments, the heat exchanger core 270 is similar to the heat exchanger core 166 discussed with respect to FIG. 4.

In use, blood enters through the blood inlet 258 and passes into the heat exchanger core 270. The blood fills the heat exchanger core 270 and exits through the three elongate core apertures 276. In some embodiments, the blood processing apparatus 250 includes an annular space 280 that collects blood exiting the heat exchanger element 272 before directing the blood towards a radially disposed shell aperture 282. As shown in FIG. 7, the presence of the annular space 280 results in a substantially radial or cross-flow blood pattern. In other words, blood will flow from the core 270 radially outward through the fibers of the heat exchanger element 272 until it reaches the annular space 280, which is located between an outer surface of the heat exchanger element 272 and an inner surface of the cylindrical shell 274. Upon reach the annular space 280, blood will accumulate and flow in a substantially longitudinal manner toward the shell aperture 282. In exemplary embodiments, the space 280 between the heat exchanger element 272 and the wall of the cylindrical shell 274 is between about 0.2 and about 1.0 mm.

Blood passing through the radially disposed shell aperture 282 passes over the gas exchanger element 276. In some embodiments, the radially disposed shell aperture 282 may be located near an end of the blood processing apparatus 250 that is opposite the blood outlet 260, thereby causing the blood flowing around and past the gas exchanger element 272 in a longitudinal direction. Blood then exits the blood processing apparatus 250 through the blood outlet 260.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A blood processing apparatus comprising:
a housing having a blood inlet and a blood outlet, the blood inlet extending into an interior of the housing;
a heat exchanger core extending coaxially within the housing and having a core interior in fluid communication with the blood inlet, the heat exchanger core including an outer surface and at least one pair of elongate core apertures formed within the outer surface, the pair of elongate core apertures configured to permit blood to pass from the core interior;
heat exchanger hollow fibers disposed about the heat exchanger core such that a heat exchanger fluid may flow through the heat exchanger hollow fibers and blood passing from the plurality of elongate core apertures may flow radially outward across the heat exchanger hollow fibers;
a cylindrical shell extending coaxially about the heat exchanger core, the cylindrical shell including a shell aperture configured to permit blood to pass to an exterior of the cylindrical shell, the shell aperture comprising a circumferentially disposed aperture disposed near an end of the cylindrical shell longitudinally opposite that of the blood inlet, such that blood entering the cylindrical shell must move with a longitudinal flow component before passing through the aperture; and
gas exchanger hollow fibers disposed about the cylindrical shell such that gases may flow through the gas exchange hollow fibers and blood passing from the shell aperture may flow across the gas exchanger hollow fibers in a longitudinal direction and towards the blood outlet.

2. The blood processing apparatus of claim 1, wherein the heat exchanger core includes three pair of elongate core apertures radially disposed at approximately equal distances about a circumference of the heat exchanger core.

3. The blood processing apparatus of claim 1, wherein the plurality of elongate core apertures are arranged in pairs.

4. The blood processing apparatus of claim 3, wherein the plurality of elongate core apertures comprise a total of four equally spaced pairs of elongate core apertures.

5. The blood processing apparatus of claim 1, wherein each pair of elongate core apertures comprise a first elongate channel and a second elongate channel separated by an elongate dividing plate extending between the first elongate core aperture and the second elongate core aperture.

6. The blood processing apparatus of claim 5, wherein each of the first and second elongate channels have a floor surface disposed at an angle with respect to a longitudinal axis of the heat exchanger core, such that a depth of each of the first and second elongate channels decreases as blood flows longitudinally along the heat exchanger core.

7. The blood processing apparatus of claim 5, wherein the outer surface of the heat exchanger core includes a plurality of radially disposed ribs.

8. The blood processing apparatus of claim 1, further comprising an annular collection space between the heat exchanger hollow fibers and the cylindrical shell, the annular collection space in fluid communication with the shell aperture.

* * * * *